United States Patent [19]
Ferrari et al.

[11] Patent Number: 5,968,825
[45] Date of Patent: Oct. 19, 1999

[54] ANTISENSE OLIGONUCLEOTIDES COMPLEMENTARY TO THE PRIMARY TRANSCRIPT OF THE HUMAN C-FES PROTOONCOGENE

[75] Inventors: Sergio Ferrari, Modena; Rossella Manfredini, Campogalliano, both of Italy

[73] Assignee: Istituto Biochimico Italiano Giovanni Lorenzini S.P.A., Milan, Italy

[21] Appl. No.: 08/859,389

[22] Filed: May 20, 1997

[30] Foreign Application Priority Data

May 20, 1996 [IT] Italy .................................. MI96A1011

[51] Int. Cl.⁶ .............................. C12Q 1/68; C07H 21/04
[52] U.S. Cl. ............................ 435/375; 435/6; 435/91.1; 435/325; 435/366; 435/372.1; 435/375; 435/440; 536/23.1; 536/24.31; 536/24.33; 536/24.5
[58] Field of Search ......................... 435/6, 91.1, 172.1, 435/172.3, 325, 366, 375, 440, 372.1; 536/23.1, 24.5, 24.1, 24.33, 24.31; 514/44

[56] References Cited

PUBLICATIONS

Frankel et al., "The Retinoic Acid Syndrome in Acute Promyelocytic Leukemia", American College of Physicians, 1992, pp. 292–296.

Dubois et al., "Modulation of IL–8, IL–1β, and G–CSF Secretion by All–Trans Retinoic Acid in Acute Promyelocytic Leukemia", Leukemia, vol. 8, No. 10, Oct. 1994, pp. 1750–1757.

Grande et al., "All–trans–retinoic acid induces simultaneously granulocytic differentiation and expression of inflammatory cytokines in HL–60 cells", Experimental Hematology, vol. 23, 1995, pp. 117–125.

Miller et al., "Anticode Oligonucleoside Methylphosphonates and Their Psoralen Derivatives", Antisense Research and Applications, 1993, pp. 189–203.

Citro et al., "Inhibition of leukemia cell proliferation by receptor–medicated uptake of c–myb antisense oligodeoxynucleotides", Proc. Natl. Acad. Sci., vol. 89, Aug. 1992, pp. 7031–7035.

Ferrari et al., "Expression of human c–fes onc–gene occurs at detectable levels in myeloid but not in lymphoid cell populations", British Journal of Haematology, 1985, vol. 59, pp. 21–25.

Castaigne et al., "All–Trans Retinoic Acid as a Differentiation Therapy for Acute Promyelocytic Leukemia. I. Clinical Results", Blood, vol. 76, No. 9, Nov. 1990, pp. 1704–1709.

Alcalay et al., "Characterization of human and mouse c–fes cDNA clones and identification of the 5' end of the gene", Oncogene, 1990, vol. 5, pp. 267–275.

Delva et al., "Resistance to All–Trans Retinoic Acid (ATRA) Therapy in Relapsing Acute Promyelocytic Leukemia: Study of In Vitro ATRA Sensitivity and Cellular Retinoic Acid Binding Protein Levels in Leukemic Cells", Blood, vol. 82, No. 7, Oct. 1993, pp. 2175–2181.

Ferrari et al., "Expression of the Myeloperoxidase Gene in Acute and Chronic Myeloid Leukemias: Relationship to the Expression of Cell Cycle–Related Genes", Leukemia, vol. 13, No. 6, Jun. 1989, pp. 423–430.

Ferrari et al., "Expression of Growth–regulated Genes in Human Acute Leukemias", Cancer Research 46, Oct. 1986, pp. 5162–5166.

Zeleznik–Le et al., "The Molecular Biology of Myeloproliferative Disorders as Revealed by Chromosomal Abnormalities", Seminars in Hematology, vol. 32, No. 3, Jul. 1995, pp. 201–219.

Ferrari et al. "Proliferation, Differentiation Arrest, and Survival in Leukemic Blast Cells", New York Academy of Sciences, vol. 663, Nov. 1992, pp. 202–214.

Gewirtz et al. PNAS 93:3161–3163 (1996).

Rojanasakul Adv. Drug Delivery Reviews 18(1996) 115–131.

Ferrari et al. Cell Growth and Differentiation 1:543–548, Nov. 1990.

Ferrari et al. Leukemia 8(Suppl. 1) 1994. 591–594.

Manfredini et al. Blood 89(1):135–145, Jan. 1, 1997.

Manfredini et al. J. Exp. Med. 178:381–389, Aug. 1993.

Ferrari et al. Proceedings Amer. Assoc. Cancer Res. 34. 1993. 94.

*Primary Examiner*—John L. LeGuyader
*Attorney, Agent, or Firm*—McDermott, Will & Emery

[57] ABSTRACT

The following description sets forth antisense (AS) oligonucleotides (ODNs) complementary to the primary transcript of the human c-fes protooncogene and their use to inactivate said transcript. All-trans retinoic acid (ATRA) is reported to be used as a differentiation inducer on cells pretreated with said AS-ODNs to induce apoptosis of leukemic blast cells.

9 Claims, 5 Drawing Sheets

Fig. 2

| SEQ ID NO: | Oligomer | Sequence (5'-3') | Mer | Target | Region |
|---|---|---|---|---|---|
| 3 | FES-S-sj1 | CAGCCCCATCAGTCAGGTCAGGTGGGTCTCTATGGGAC | 33 | Splice junction exon2/intron 2 | 1211-1243 ‡ |
| 4 | FES-IP-sj1 | GTCGGGGTAGTCAGTCAGTCCACCCAGAGATACCCTG | 33 | Splice junction exon2/intron 2 | 1243-1211 ‡ |
| 1 | FES-AS-sj1 | GTCCCATAGAGACCCACCTGACTGATGGGGCTG | 33 | Splice junction exon2/intron 2 | 1243-1211 ‡ |
| 5 | FES-S-sj2 | GCAGGAGCTCACCAAGGTGAGGGGCAGCACT | 32 | Splice junction exon3/intron3 | 1537-1568 ‡ |
| 6 | FES-IP-sj2 | CGTCCTCGAGTGGTTCCACTCGCCCGTCGTGA | 32 | Splice junction exon3/intron3 | 1568-1537 ‡ |
| 2 | FES-AS-sj2 | AGTGCTGCCCCGCTCACCTTGGTGAGCTCCTGC | 32 | Splice junction exon3/intron3 | 1568-1537 ‡ |

‡ GenBank, Accession Number X06292.

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (ix) FEATURE:
      (A) NAME/KEY: misc_feature
      (B) LOCATION: 1
      (D) OTHER INFORMATION: /note= "Antisense oligonucleotide
         sequence complementary to the primary transcript of c-fes
         protooncogene."

(xi) SEQUENCE DESCRIPTION: SEQ ID NO:1:

GTCCCATAGA GACCCACCTG ACTGATGGGG CTG      33

(2) INFORMATION FOR SEQ ID NO:2:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (ix) FEATURE:
      (A) NAME/KEY: misc_feature
      (B) LOCATION: 1
      (D) OTHER INFORMATION: /note= "Antisense oligonucleotide
         sequence complementary to primary transcript of the c-fes
         protooncogene."

(xi) SEQUENCE DESCRIPTION: SEQ ID NO:2:

AGTGCTGCCC GCTCACCTTG GTGAGCTCCT GC      32

(2) INFORMATION FOR SEQ ID NO:3:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (ix) FEATURE:
      (A) NAME/KEY: misc_feature
      (B) LOCATION: 1
      (D) OTHER INFORMATION: /note= "Sense labelled
         oligonucleotide sequence."

-continued (xi) SEQUENCE DESCRIPTION: SEQ ID NO:3:

CAGCCCCATC AGTCAGGTGG GTCTCTATGG GAC                    33

(2) INFORMATION FOR SEQ ID NO:4:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (ix) FEATURE:
       (A) NAME/KEY: misc_feature
       (B) LOCATION: 1
       (D) OTHER INFORMATION: /note= "Inverted polarity
           oligonucleotide sequence."

(xi) SEQUENCE DESCRIPTION: SEQ ID NO:4:

GTCGGGGTAG TCAGTCCACC CAGAGATACC CTG                    33

(2) INFORMATION FOR SEQ ID NO:5:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (ix) FEATURE:
       (A) NAME/KEY: misc_feature
       (B) LOCATION: 1
       (D) OTHER INFORMATION: /note= "Sense labelled
           oligonucleotide sequence."

(xi) SEQUENCE DESCRIPTION: SEQ ID NO:5:

GCAGGAGCTC ACCAAGGTGA GCGGGCAGCA CT                     32

(2) INFORMATION FOR SEQ ID NO:6:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (ix) FEATURE:
       (A) NAME/KEY: misc_feature
       (B) LOCATION: 1
       (D) OTHER INFORMATION: /note= "Inverted polarity
           oligonucleotide sequence."

(xi) SEQUENCE DESCRIPTION: SEQ ID NO:6:

CGTCCTCGAG TGGTTCCACT CGCCCGTCGT GA                     32

ANTISENSE OLIGONUCLEOTIDES COMPLEMENTARY TO THE PRIMARY TRANSCRIPT OF THE HUMAN C-FES PROTOONCOGENE

FIELD OF THE INVENTION

This invention concerns new antisense oligonucleotides complementary to the primary transcript of the human c-fes protooncogene and their use to specifically inactivate the above mentioned primary transcript. The invention also concerns the use of the differentiation inducer all-trans retinoic acid (ATRA) on cells pretreated with specific c-fes antisense oligonucleotides to induce apoptosis of leukemic blasts.

BACKGROUND OF THE INVENTION

In acute myeloid leukemia (AML), the microenvironmental control on the leukemic blast cell population is almost completely ineffective, since leukemic blast cells have acquired the characteristic of autonomy, probably due to the several genetic alterations exibited (Seminars in Hematol 32: 201–219, 1995). As demonstrated several years ago, the growth fraction of a leukemic population is extremely low because the large majority of AML blast cells do not proliferate actively. Actually, it was observed that AML blast cells are not quiescent, i.e in the Go state, but are blocked at the G1 phase of the cell cycle and loose the capability to progress through the S phase and, therefore, through the cycle (Cancer Res. 46: 5162–5166, 1986; Leukemia 3: 423–430, 1989). Leukemic blast cells accumulation in G1 determines an unbalance between the pool of cells in the cycle and the cells leaving the cycle to enter terminal differentiation. It is therefore evident that the blast cells proliferation advantage is not caused by an increased proliferative capacity, but mainly to the differentiation block, an increased half-life (approx. 25–35 days) (Eur. J. Clin. Invest., 2: 259, 1972) and to a reduced rate of apoptosis. Therefore, in acute myeloid leukemia, the high number of circulating blasts is consequent on the increased cell viability (NYAS 663: 202–214, 1992). Ferrari et al. (British J. Haematol 59: 21–25, 1985) found that the c-fes protooncogene is expressed at high levels in the terminal stages of granulocytic differentiation, but no function could be attributed to the product of this protooncogene. Ferrari et al (Cell growth Diff. 1: 543–548, 1990) and Manfredini et al. (J.Exp.Med., 178: 381–389, 1993) also found that the inhibition of the c-fes protooncogene expression could be obtained by antisense oligodeoxynucleotides (AS-ODNs) specific for c-fes protooncogene mRNA. However, the use of AS-ODNs specific for mRNA have some inconveniences, in particular a scarce inactivation efficiency. Acute promyelocytic leukemia (APL) blast cells can be induced to differentiation, in vivo and in vitro, with all-trans retinoic acid (ATRA) (New Engl. J. Med., 234: 1385, 1991). At present, ATRA is used in vivo for therapeutic purposes to obtain APL blasts differentiation. However, along with the differentiating effect, some untoward side effects, e.g. leukocytosis (Blood, 76: 260, 1990) and the capillary permeability syndrome (Am. Int. Med., 117: 292, 1992) are observed. This syndrome, characterized by acute pulmonary edema, renal insufficiency, hypotension, was first observed in patients treated with IL-2. Endothelial injury and leukocytes infiltration of the surrounding tissue are observed in the capillary permeability syndrome. Some authors propose the hypothesis that inflammatory cytokines, such as IL-1, IL-6, IL-8 and TNFα on one hand (Leukemia, 8: 1750, 1994; Exp. Hematol. 23: 117–125, 1995) and integrines on the other hand may play a role in the pathogenesis of the capillary permeability syndrome. In fact, ATRA has been shown to cause APL blasts activation, and the consequent induction of the expression of inflammatory cytokines (Exp. Hematol., 23: 117, 1995). Differentiation therapy has to last some months, during which complications jeopardizing the treatment efficacy often arise. As already mentioned, one of the most serious inconveniences produced by a long-term treatment with ATRA is the onset in approx. 20% of cases of the capillary permeability syndrome (often associated to severe leukocytosis). These side effects of ATRA therapy can lead to the interruption of treatment or even to the patient's death. A further inconvenience often arising during a long-term differentiating treatment with ATRA is the onset of a drug resistance mechanism, whereby the treatment obviously becomes ineffective (Blood 82: 2175–2181, 1993). It is, therefore, extremely important to find new products or develop new therapeutic strategies, capable of avoiding the aforementioned drawbacks, or improve the products already known, for an adjuvant treatment of leukemia.

SUMMARY

It has surprisingly been found that new antisense (AS) oligodeoxynucleotides (ODNs) capable of hybridizing with the primary transcript (hn-RNA) of the c-fes protooncogene provide a better inactivation of the c-fes protooncogene and allow the elimination of the drawbacks inherent in the systems known in the art. It is, therefore, an aspect of the present invention to provide said new AS-ODNs or mixtures thereof, useful to inactivate the primary transcript of the c-fes protooncogene. The present invention also relates to ATRA as a differentiation inducer on cells pretreated with the AS-ODNs of the invention to produce a rapid apoptosis (cell death) (24 to 72 h). The present invention also relates to a therapeutical composition comprising at least one of the AS-ODNs according to the invention and ATRA. It is a further feature of the invention to provide a therapeutic treatment consisting of a pretreatment with the AS-ODNs of the invention and of ATRA administration to induce a rapid apoptosis of leukemic cells. Furthermore, the present invention relates to a kit including one or more phials of AS-ODNs according to the invention and one or more phials of ATRA.

DESCRIPTION OF THE FIGURES AND SEQUENCES

FIG. 1 shows the genetic locus of the c-fes protooncogene and the relevant oligonucleotides exemplified in the invention (reported in SEQ ID NO: 1 and SEQ ID NO: 2). The two AS-ODNs complementary to 5' splice junction between exon 2 and intron 2, and between exon 3 and intron 3, are denominated FES-AS-sj1 and FES-AS-sj2

FIG. 2 shows FES-AS-sj1 and FES-AS-sj2 as per FIG. 1 and the corresponding sense labelled (FES-S) and inverted polarity (FES-IP) control oligomers.

FIG. 3 reports the detection by RT-PCR technique of FES-AS-sj1 and 2 of FIGS. 1 and 2 and of the relevant controls. For the experiment completeness, also the AS-ODNs complementary to mRNA according to Manfredini et al. (cf. State of the art), denominated S(mRNA), IP(mRNA) and AS(mRNA), were assayed. Lane 1: DNA marker VIII (Boehringer, Mannheim, Germany); Lane 2: untreated HL60 cells; Lane 3: HL60 cells treated with the FES-S-sj1 and 2 [S(sj)] mixture; Lane 4: HL60 cells treated with the FES-IP-sj1 and 2 [IP(sj)] mixture; Lane 5: HL60 cells treated with the FES-AS-sj1 and 2 [AS(sj)] mixture; Lane 6: HL60 cells treated with a mixture of FES-S [S(mRNA)]; Lane 7: HL60 cells treated with a mixture of FES-IP [IP(mRNA)]; Lane 8: HL60 cells treated with a mixture of FES-AS [AS(mRNA)]; Lane 9: negative control on genomic DNA of HL60 cells; Lane 10: negative control conducted without cDNA template.

FIGS. 4A–4C report the detection by Western blot analysis of the p92c-fes protein in HL60 cells treated with the c-fes ODN. Terms are as used in FIG. 3 SEQ ID NO: 1 refers to an antisense oligonucleotide, specific for the primary transcript of the human c-fes protooncogene, and corresponding to the 5' region of exon 2/intron 2 junctions and, with reference to the published gene sequence (Oncogene, 5: 267, 1990) corresponding to residues 1211–1243 of said protooncogene. SEQ ID NO: 2 refers to an antisense oligonucleotide, specific for the primary transcript of the human c-fes protooncogene, and corresponding to the 5' region of exon 3/intron 3 junctions and, with reference to the published gene sequence, corresponding to residues 1537–1568 of said protooncogene.

DETAILED DESCRIPTION OF THE INVENTION

Figure 1:
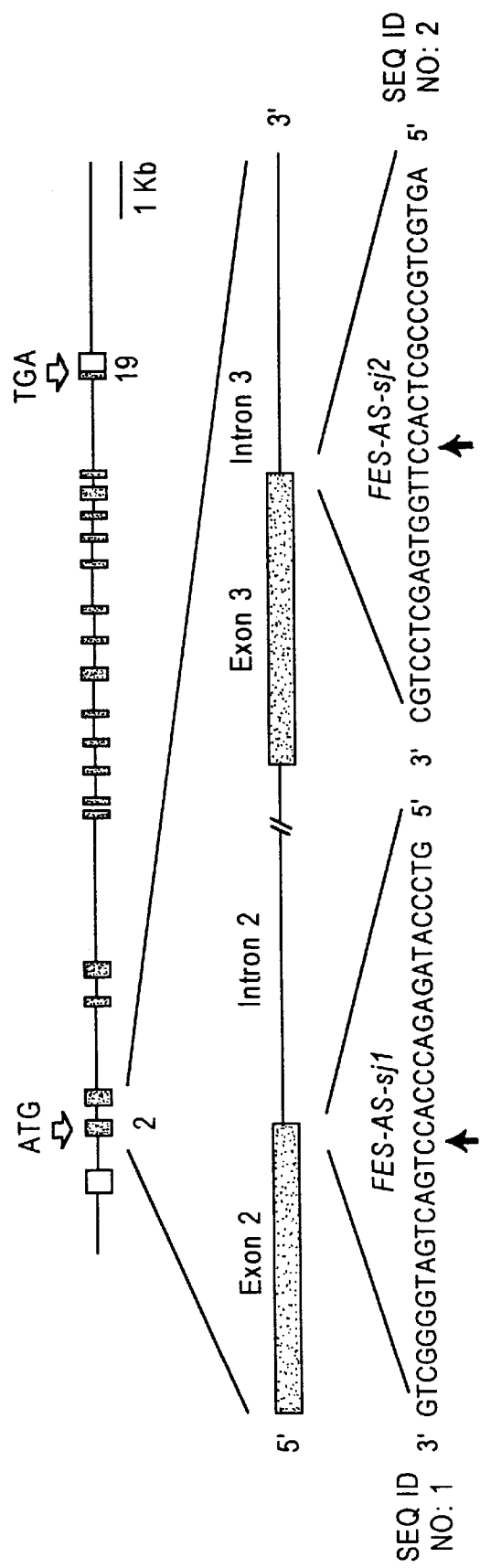

For better understanding of the invention, the description reported herein is furnished with figures and nucleotide sequences. The new antisense oligonucleotides according to the invention include all oligonucleotides complementary to the primary transcript (i.e. hn-RNA) of the c-fes protooncogene, which, therefore, inhibit production of the c-fes protein, particularly the AS-ODNs of length varying from 16 to 40 nucleotides and more particularly the AS-ODNs consisting of 32–33 nucleotides. Preferred AS-ODNs are those described in FIGS. 1 and 2, with sequences 5'-GTCCCATAGAGACCCACCTGACTGA TGGGGCTG-3' (SEQ ID NO: 1) and 5'-AGTGCTG CCCGCTCACCTTGGTGAGCTCCTGC-3' (SEQ ID NO: 2). Said AS-ODNs were found at the two 5' regions of exon 2/intron 2 and exon 3/intron 3 junctions, respectively. With reference to the gene sequence, said regions correspond to residues 1211–1243 and 1537–1568, respectively (Oncogene, 5: 267, 1990). The oligonucleotides of the invention can be prepared by known methods, e.g. as described in Cell Growth Diff., 1: 543 (1990). The oligonucleotides of the invention are preferably stabilized by structural modifications, with a view to prolonging their half-life. Said modifications especially but not exclusively concern the internucleotide phosphate bridge, which can be transformed into methylphosphonate-, phosphorothionate- or phosphorodithionate-group, phosphate esters, etc. (Antisense Research and Applications, Crooke and Lebleu, eds., CRC Press, p. 189–205, 1993). In particular, particularly preferred are the derivatives substituted, at the 3' and 5' end points, with phosphorothionate residues. The oligonucleotides of the invention may also be complexed non-covalently with a transferrin-polylysine conjugate (Natl. Acad. Sci. USA, 89: 7031, 1991). Consequently, they are transported more easily through cell membranes and then divide into active oligonucleotides in the cytoplasmatic vesicles having acid pH. The transport through cell membranes may also be obtained by means of liposomes. It has been found that also a mixture of AS-ODNs according to the invention effectively allows the inhibition of the c-fes primary transcript. For the therapeutic uses envisaged, in particular for an adjuvant treatment of acute promyelocytic leukemia, the present invention also includes pharmaceutical compositions containing the AS-ODNs of the invention as active ingredients, either alone or in combination with a vehicle suitable for oral or parenteral administration. In particular, the AS-ODNs of the invention may be administered, either alone or in the form of a mixture, during treatment with a differentiation inducer of APLs, to avoid side effects, such as leukocytosis and the capillary permeability syndrome. The compositions of the invention, prepared by conventional methods, may be provided in the form of a commercial kit including, for human use, the following components and quantities:

i) one or more phials, depending on the days and on the number of administrations, each containing 100 to 500 mg of one of the two AS-ODNs of the invention or of a mixture thereof, to be administered daily in the first days of pretreatment. The aforesaid quantities will depend on the patient's body surface.

ii) one or more phials, as reported above, each containing 100 to 500 mg of at least one of the two AS-ODNs of the invention and one or more phials containing 5 to 50 mg ATRA, to be administered daily in the successive days of treatment.

For an adult patient, the kit will preferably include:

i) 10 phials, each containing 500 mg of an equimolar mixture of the two AS-ODNs SEQ ID NO:1 and SEQ ID NO:2 to be administered twice a day during the first 5 days of pretreatment;

ii) 6 phials, each containing 500 mg of an equimolar mixture of said two AS-ODNs, and 6 phials, each containing 50 mg ATRA, to be administered, approximately at the same moment, twice a day in the successive 3 days of treatment.

In the treatment phase, instead of administering AS-ODNs and ATRA separately, it is possible to administer a mixture of at least one AS-ODN and ATRA. Therefore, the kit of the invention may, in phase ii), include one or more phials, each containing at least one of the AS-ODNs (100 to 500 mg) combined with ATRA (5 to 50 mg). The authors of the present invention have found that, when ATRA was administered on APL cells pretreated with the AS-ODNs of the invention, a rapid cell apoptosis took place. Unlike the knowledge acquired in the prior art, i.e. that ATRA administration to cells having promyelocytic phenotype induced differentiation (followed by apoptosis) within a fairly long time, i.e. 6 to 9 days, the administration of a differentiation inducer (preferably ATRA) to cells pretreated with the AS-ODNs of the invention induces a rapid apoptosis, i.e. within 24 to 72 h. The present invention also includes the treatment of patients with APL according to the aforementioned procedure. In fact, whereas ATRA administration to patients with APL induces differentiation (followed by apoptosis) within a fairly long time (9 to 12 days), the inducer administration to patients pretreated with the AS-ODNs of the invention induces a very rapid apoptosis (within 24 to 72 h), with leukemic clone eradication within a much shorter time. Salient among the advantages of the present invention is the possibility of inducing leukemic blasts apoptosis in time for preventing the onset of the aforesaid side effects arising from the treatment with ATRA: said strategy might represent a valid supporting treatment of APL.

It is therefore an object of the invention to provide a therapeutic method for the treatment of leukemia, comprising administering at least one antisense oligonucleotide of the invention, followed by administering all-trans retinoic acid to induce cell apoptosis. Said therapeutic method preferably comprises:

administering 100 to 500 mg of at least one of said antisense oligonucleotides, twice a day for 5 days;

administering 100 to 500 mg of at least one of said antisense oligonucleotides in association with 5 to 50 mg of all-trans retinoic acid, twice a day for 3 days.

A particular embodiment of the present invention is described in the following example.

EXAMPLE

Treatment of HL60 Cells and APL Blasts with a Mixture of the claimed AS-ODNs

Figure 3:
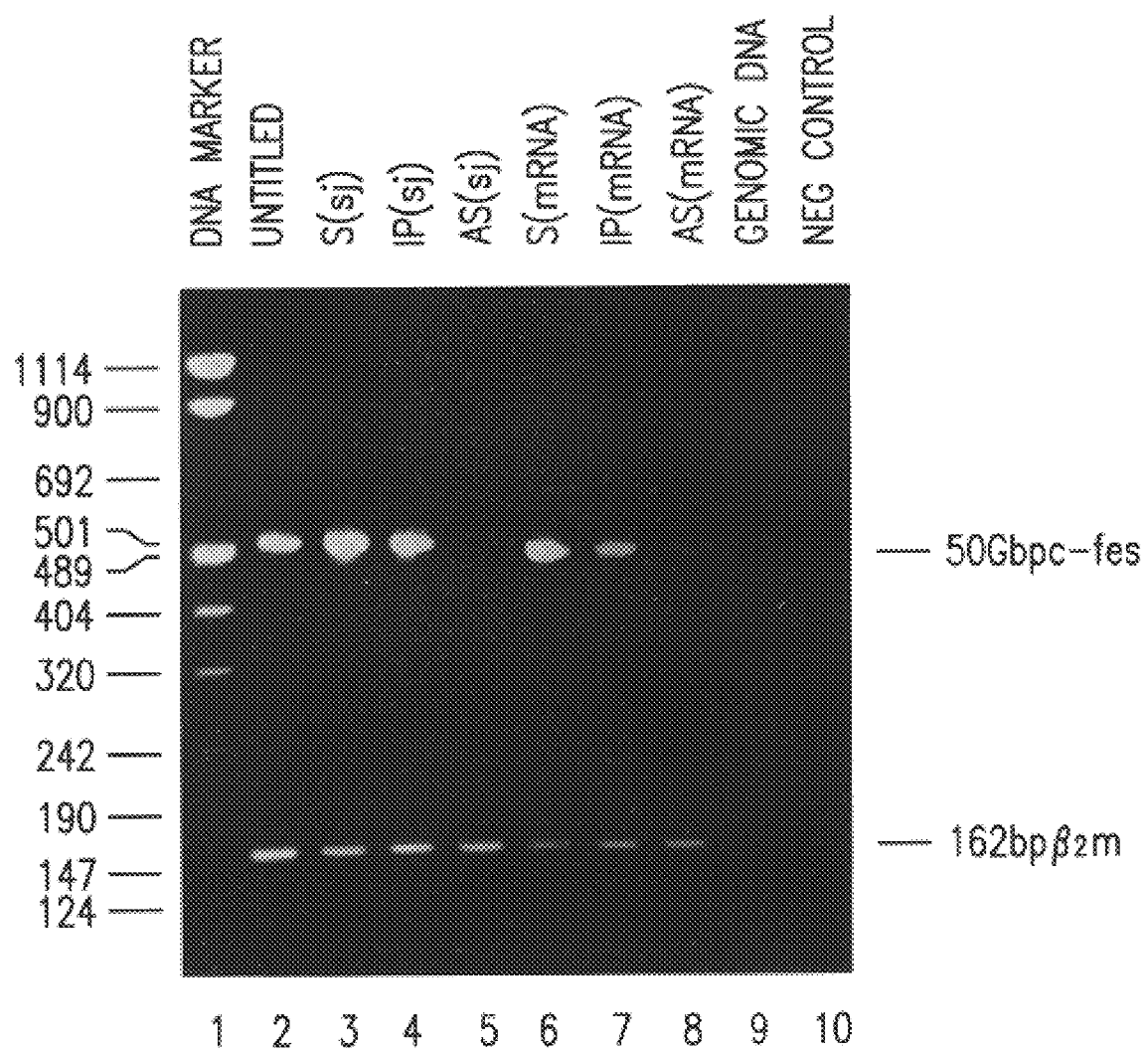
Figure 4A:
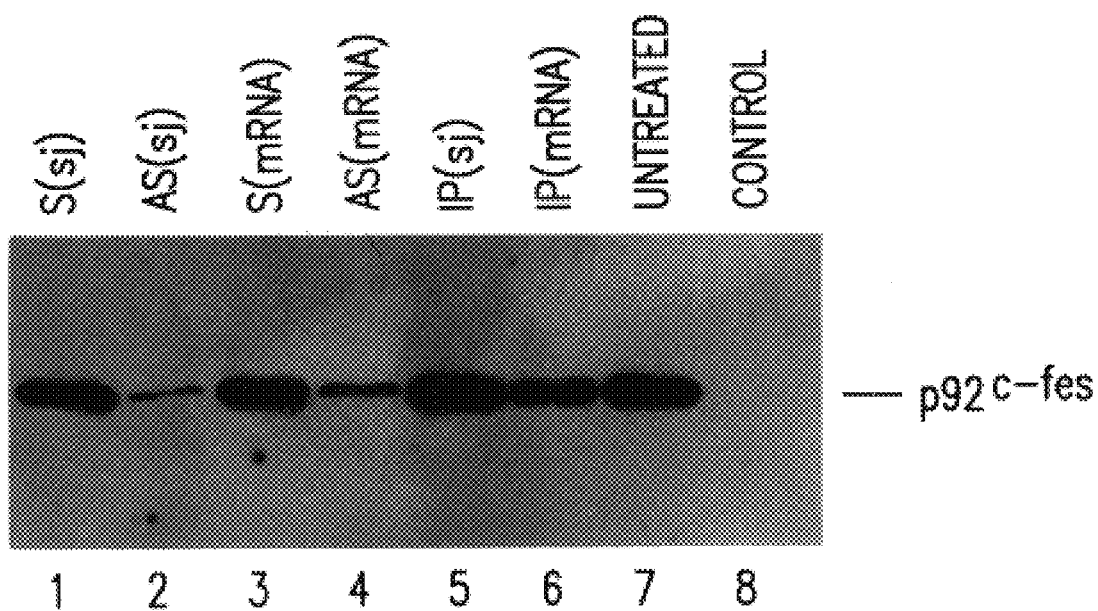
Figure 4B:
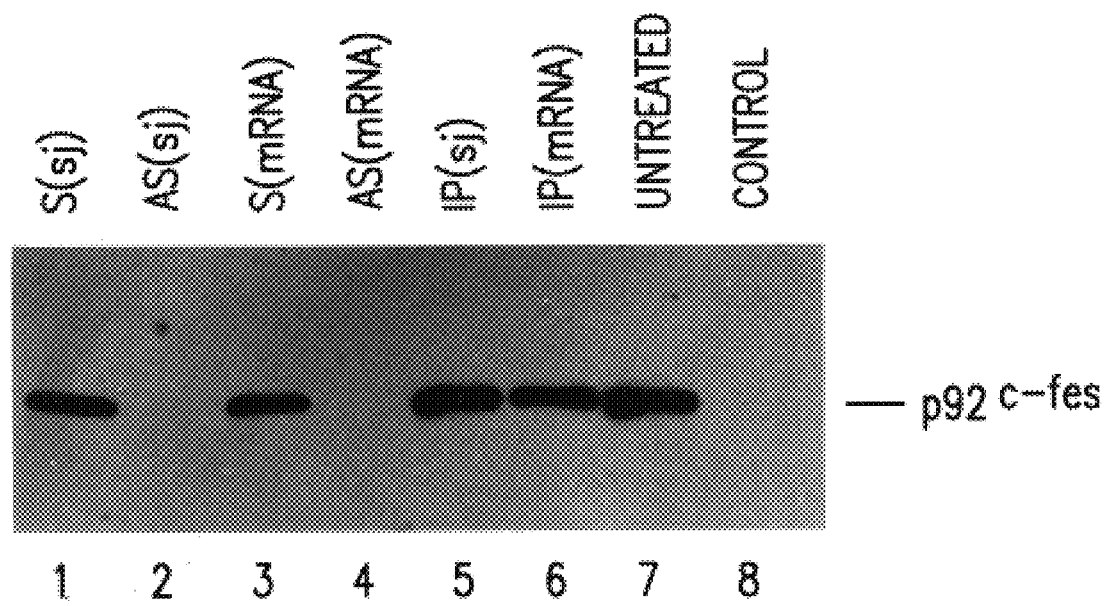
Figure 4C:
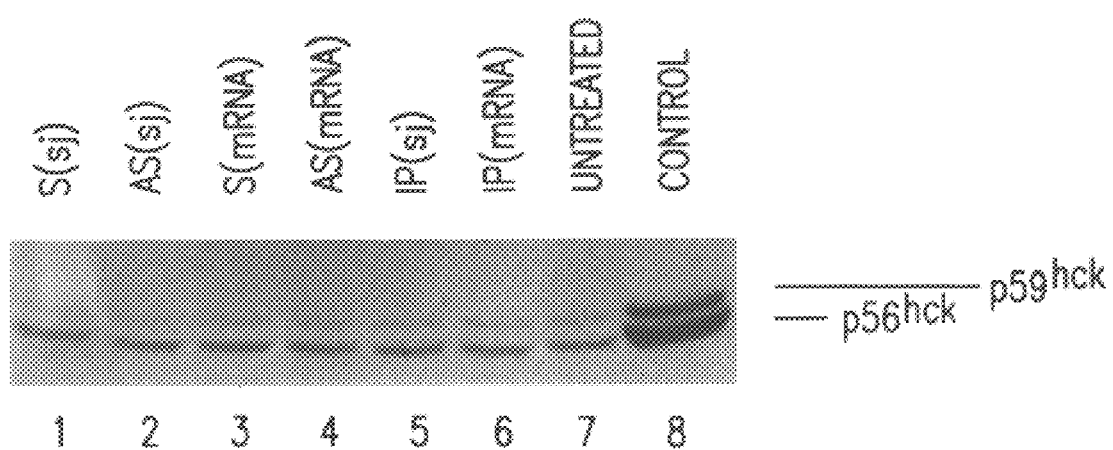

The two nonmodified oligodeoxynucleotides shown in SEQ ID NO:1 and SEQ ID NO: 2 were synthesized on an automated solid-phase DNA synthesizer (Mod. 394, Applied Biosystems Inc.). Said oligomers were purified by extraction (3 to 4 times with NH4OH) followed by incubation for 16 h at 56° C., and by precipitation with ethanol or by PAGE (Cell Growth Diff., 1: 543, 1990). The oligomers used in gene inactivation strategy were lyophilized and resuspended in cell culture medium prior to use. The oligomers synthesized had been previously compared with the NIH genomic data bank (Software Dnasis, Hitachi, Brisbane, Calif., USA) to exclude homology between the oligomers and other known sequences greater than 70%. Once the oligomers' stability in the culture medium had been checked, HL60 cells were incubated with 10 uM AS-ODN mixture in microwells, each containing 7×105 cells/ml in RPMI 1640 supplemented with 10% heat-treated Fetal Calf Serum (FCS) (previously selected for minimal nuclease activity) and with 2 mM L-glutamine. APL blasts, highly homogeneous as to leukemic cells % amount and exhibiting the typical t(15;17) (i.e. the translocation between human chromosome 15 and chromosome 17) involving PML and RARa genes were cultured under the same conditions. AS-ODNs were added to the cultures every 24 h to maintain a constant concentration of approx. 10 $\mu$M. Some cell aliquots were collected at 24-h intervals to evaluate the kinetics of disappearance of c-fes mRNA and protein. Studies of the messenger expression carried out by Reverse Transcription-Polymerase Chain Reaction (RT-PCR) established that after 96 h of treatment with AS-ODNs, there was a sharp decrease in c-fes mRNA levels, which were no longer detected after 96 h of treatment with both inactivation strategies (FIG. 3). The expression of the c-fes protein (i.e. the p92c-fes protein) determined by Western blot, substantially decreased after 72 h of treatment and disappeared completely after 120 h (FIG. 4). Cell death, determined by the trypan blue exclusion test, was lower than 5%. Once HL60 cells and APL blasts had been pretreated with 10 $\mu$M AS-ODNs (i.e. once the protein of said protooncogene had been completely inactivated), the cells were induced to differentiate by treatment with 1 uM ATRA (always in the presence of AS-ODNs). The results obtained show that these cells are incapable of progressing along the granulocytic differentiating pathway.

A. Morphological and Flow Cytometric Analyses

Although maintaining the characteristics of immaturity, the cells began to die after a few hours, and >50% of cell death was observed after 24 h. At 48 h from the induction with ATRA and AS-ODNs, the amount of dead cells increased to 70% to reach 90% after 120 h. The morphology of said cells observed day after day showed the typical modifications induced by an apoptotic process: cytoplasmatic and nuclear condensation (pycnosis), nuclear fragmentation (karyorrhexis) with formation of vesicles containing coarctate material, phagocyted by surrounding cells. The presence and progression of the apoptotic process was characterized by subjecting various aliquots of untreated and oligomer-treated cells to monoparametric flow cytometric analysis for the determination of the DNA content, every 24 h after induction with ATRA, using a FACScan (Becton Dickinson).The flow cytometric analysis of AS-ODN pretreated cells revealed, already 24 h from induction with ATRA, the appearance of a hypodiploid fluorescence peak, corresponding to the DNA of the apoptotic population. During the successive days, the hypodiploid peak gradually increased until an almost total disappearance of peaks 2C and 4C (diploid content) at 72 h after induction with ATRA, with the apoptotic cells amounting to 97 to 98%. The same analysis conducted on cells either untreated or treated with control oligomer showed the presence only of fluorescence peaks 2C and 4C, which proved the integrity of the population DNA and, therefore, the specificity of the AS-ODN effect. No granulocytic maturation characteristics were observed before death: this seems to exclude the possibility that treatment with AS-ODNs simply enhances the granulocytic differentiation process. Therefore, the progressive cell death completely hinders differentiation to granulocytes. Control oligomers do not absolutely interfere with ATRA-induced granulocytic differentiation, which, as demonstrated by the morphological and flow cytometric analyses, takes place without a significant cell death B. DNA Molecular Analysis In ATRA- and AS-ODN-treated cells, DNA fragmentation produces multimers of approx. 185 to 200 base pairs (bp) synchronously with the compaction of chromatin, observed morphologically. This characteristic "ladder" fragmentation pattern was evidenced in DNA extracted from cells after 24 h and 48 h of treatment with AS-ODNs and ATRA. Conversely, high molecular weight DNA was found in cells treated with inducer alone or in combination with control oligomers.

C. Effects of Hematopoietic Growth Factors on Cell Death Induced After c-fes Inhibition and Treatment with ATRA IL-3, IL-6, SCF, GM-CSF and G-CSF were tested to examine their ability to compete with the apoptotic process induced after c-fes inactivation during granulocytic differentiation. After c-fes inactivation by AS-ODNs, the following cytokines, i.e. IL-3 (5 ng/ml), IL-6 (10 U/ml), Stem Cell Factor (SCF, 10 ng/ml), GM-CSF (20 ng/ml), G-CSF (1000 U/ml), were added simultaneously with ATRA addition and in the presence of AS-ODNs. As revealed by flow cytometric analysis carried out as described above, IL-3, IL-6 and SCF do not produce any protective effect. Conversely, by addition of GM-CSF and, respectively, of G-CSF, approx. 70% of cells was protected, the protection lasting for more than 3 days: actually, after 120 h of treatment, more than 40% of cells was still viable. Each experiment was repeated 3 times and the variability was never >10%. Instead, the treatment with IL-3, IL-6 and SCF did not result in any protective effect. The data obtained show that the induction to granulocytic differentiation, after complete inhibition of the c-fes function, leads to a gradual cell death, the HL60 cells and APL blasts being incapable of completing said differentiating programme. Therefore, it was demonstrated that the cell viability loss taking place under said conditions is due to the activation of the process of programmed cell death rather than to an accelerated differentiation. In fact, cytocentrifugates prepared at various time intervals (from 24 h to 96 h) of treatment with AS-ODNs and ATRA never revealed the presence of cells with mature granulocytic phenotype. Cytochemical assays did not reveal any sign of granulocytic or monocytic maturation. The morphological and molecular aspects of the effect of c-fes inhibition in differentiating APL blasts and HL60 cells suggest that the premature cell death is a consequence of the apoptotic process activation. This conclusion is strongly supported by the fact that GM-CSF and G-CSF promote cell survival in differentiating APL blasts and HL60 cells, inferfering with the inactivation of said protooncogene and, therefore, suppressing apoptosis, even if the molecular mechanism involved in the apoptotic process induced by c-fes inhibition is still to be clarified.

We claim:

1. An antisense oligonucleotide complementary to the primary transcript of human c-fes protooncogene, which hybridizes to said primary transcript at a sequence spanning to the exon 2/intron 2 or the exon 3/intron 3 splice junction.

2. The antisense oligonucleotide of claim 1, which includes the sequence shown in SEQ ID NO:1 or SEQ ID NO:2.

3. The antisense oligonucleotide of claim 1, which is modified and stabilized to prolong its half-life.

4. The antisense oligonucleotide of claim 3, modified at its 3' or 5' end with a phosphorothionate derivative.

5. The antisense oligonucleotide of claim 3, wherein its internucleotide phosphate bridge is a methylphosphonate, phosphorothionate, phosphorodithionate, or phosphate ester group.

6. The antisense oligonucleotide of claim 3, which is complexed noncovalently with transeferrin-polylysine.

7. A method for inhibiting expression of c-fes protein in a cell comprising administering to the cell at least one antisense oligonucleotide complementary to the primary transcript of the human c-fes protooncogene, wherein said antisense oligonucleotide hybridizes with said primary transcript at a sequence spanning to the exon 2/intron 2 or the exon 3/intron 3-splice junction.

8. The method of claim 7, wherein said antisense oligonucleotide includes the sequence shown in SEQ ID NO:1 or SEQ ID NO:2.

9. The method of claim 7, further comprising administering to said cells all-trans retinoic acid to induce cell differentiation and apoptosis.

* * * * *